United States Patent [19]

Zimmerer

[11] Patent Number: 4,657,537
[45] Date of Patent: Apr. 14, 1987

[54] DISPOSABLE ABSORBENT ARTICLES

[75] Inventor: Roger E. Zimmerer, Cincinnati, Ohio

[73] Assignee: The Procter & Gamble Company, Cincinnati, Ohio

[21] Appl. No.: 895,527

[22] Filed: Aug. 11, 1986

Related U.S. Application Data

[63] Continuation of Ser. No. 734,425, May 15, 1985, abandoned.

[51] Int. Cl.$^4$ .............................................. A61F 13/16
[52] U.S. Cl. ..................................................... 604/360
[58] Field of Search ............... 604/358, 359, 360, 367, 604/368, 374–378

[56] References Cited

U.S. PATENT DOCUMENTS

| | | | |
|---|---|---|---|
| 3,004,895 | 10/1961 | Schwartz | 167/84 |
| 3,067,745 | 12/1962 | Burgeni et al. | 128/285 |
| 3,658,790 | 4/1972 | Bernardin | 260/219 |
| 3,691,154 | 9/1972 | Bernardin | 260/219 |
| 3,707,148 | 12/1972 | Bryce . | |
| 3,793,299 | 2/1974 | Zimmerer | 260/2.2 R |
| 3,794,034 | 2/1974 | Jones, Sr. | 604/360 |
| 3,804,094 | 4/1974 | Manoussos et al. | 128/290 R |
| 3,843,701 | 10/1974 | Wortham | 260/448 R |
| 3,889,678 | 6/1975 | Chatterjee et al. | 128/284 |
| 3,920,015 | 11/1975 | Wortham | 128/284 |
| 3,935,862 | 2/1976 | Kraskin | 128/287 |
| 3,964,486 | 6/1976 | Blaney | 604/360 |
| 4,020,271 | 4/1977 | Chatterjee | 536/88 |
| 4,055,184 | 10/1977 | Karami | 128/287 |
| 4,066,584 | 1/1978 | Allen et al. | 260/17.4 CL |
| 4,363,322 | 12/1982 | Anderson | 604/360 |

FOREIGN PATENT DOCUMENTS

| | | |
|---|---|---|
| 45057 | 3/1982 | Japan . |
| 748135 | 4/1956 | United Kingdom . |

OTHER PUBLICATIONS

Nite Comfort TM Diaper Rash Buffer, undated product brochure.
Kaj Health Products, Inc., Press Release, "To Control & Prevent Diaper Rash", May 13, 1985.
*The Newton Kansan*, "Distribution Ready", Sep. 8, 1984.

*Primary Examiner*—John D. Yasko
*Attorney, Agent, or Firm*—George W. Allen; Steven J. Goldstein; Richard C. Witte

[57] ABSTRACT

Disposable absorbent articles having an ion-exchanging topsheet are disclosed. By using topsheets which release protons upon exposure to body fluids, absorbent articles such as diapers can be realized which are effective for absorbing discharged body waste and which also are effective for lowering skin pH within the acid range. Lowering of skin pH to values within the range of from about 3.0 to 5.5, can serve to prevent or reduce diaper rash.

20 Claims, 1 Drawing Figure

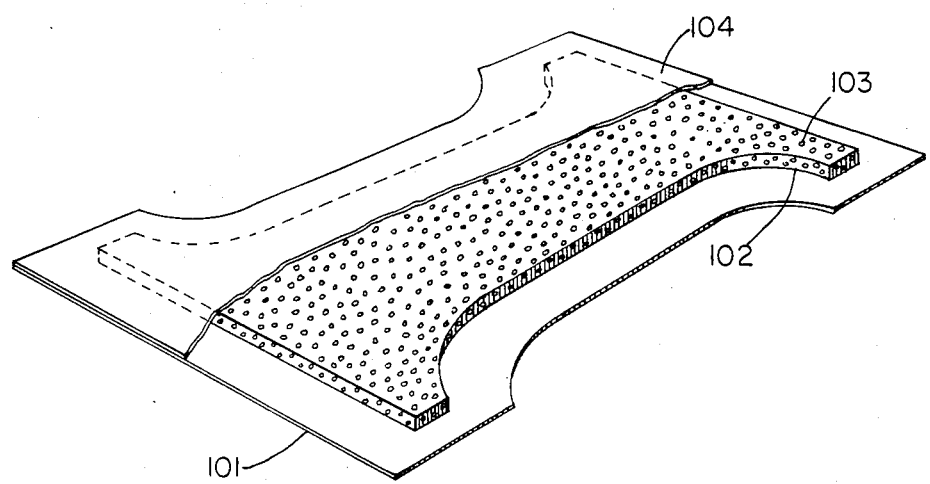

DISPOSABLE ABSORBENT ARTICLES

This is a continuation of application Ser. No. 734,425, filed May 15, 1985 now abandoned.

FIELD OF THE INVENTION

The present invention relates to disposable absorbent articles such as diapers, incontinence pads, sanitary napkins and the like. Such articles are assembled in a manner which renders them especially effective for absorbing discharged body fluids while at the same time lowering and preferably maintaining skin pH within the acid range.

BACKGROUND OF THE INVENTION

Diaper rash is a common form of irritation and inflammation of those parts of an infant's body normally covered by a diaper. It frequently occurs also in areas immediately adjacent to the diapered area. This condition is also referred to as diaper dermatitis, napkin dermatitis, napkin rash, and nappy rash. While certainly more common in infants, this condition is not, in fact, limited to infants. Any individual who suffers from incontinence may develop this condition. This ranges from newborns, to the elderly, to critically ill or nonambulatory individuals.

It is generally accepted that true "diaper rash" or "diaper dermatitis" is a condition which is, in its most simple stages, a contact irritant dermatitis. The irritation of simple diaper rash results from extended contact of the skin with urine, or feces, or both. Diapers are worn to catch and hold the body waste, but generally hold the waste in direct contact with the skin until changed, i.e., in occluded fashion for long periods of time. The same is true for an incontinence pad, or incontinence brief. However, while it is known that the body waste "causes" diaper rash, the precise component or components of the urine or feces which are responsible for the resulting irritation of the skin have not been conclusively identified. The most commonly accepted list of factors linked to diaper rash includes ammonia, bacteria, the products of bacterial action, urine pH, *Candida albicans,* and moisture. These are generally cited in the art as being the most likely candidates for agents or conditions which product or aggravate diaper rash.

It has now been discovered that a primary cause of diaper rash is a particular set of conditions which arises as a result of prolonged contact of skin with mixtures of feces and urine. Activity of proteolytic and lipolytic fecal enzymes present in such a mixture is believed to be a major factor in producing skin irritation. Urine in contact with enzymes from feces can also result in production of ammonia which raises skin pH. This rise in skin pH, for example to levels of 6.0 and above, in turn increases that fecal proteolytic and lipolytic enzymatic activity which produces diaper rash. Urine itself can also contribute to diaper rash by adding moisture to the diaper environment. Water, and particularly water in the form of urine, is especially effective at diminishing the barrier property of skin, thereby enhancing the susceptibility of skin to fecal enzyme irritation.

The foregoing diaper rash model suggests that effective diaper rash control can be achieved by lowering skin pH to values well within the acidic range to inhibit irritation-producing enzymatic activity while simultaneously maintaining the diaper environment as dry as possible. Lowering of skin pH may also be an important factor in providing rash or odor control in other types of absorbent articles such as sanitary napkins.

Articles, compositions and procedures which inherently tend to lower the pH of diapered skin are known in the art. In fact, a number of prior art references teach the addition of various acidic pH control or "ammonia-absorbing" agents to absorbent articles or to the diapered skin environment. Such references include, for example, Alonso et al., U.S. Pat. No. 4,382,919, Issued May 10, 1983; Blaney, U.S. Pat. No. 3,964,486, Issued June 22, 1976; Bryce, U.S. Pat. No. 3,707,148, Issued Dec. 26, 1972; and Jones, Sr., U.S. Pat. No. 3,794,034, Issued Feb. 26, 1974.

In those instances in the prior art wherein acidic pH control agents have been icorporated into the cores of absorbent articles, significant amounts of acid are needed in order to bring about the desired "absorption" of ammonia or lowering of skin pH. Protons released by acid material in an absorbent structure core must be carried to the skin by the relatively inefficient mechanism of back diffusion or re-wetting of the skin with fluid such as urine. In those instances wherein acidic material is carried on or in topsheets of prior art absorbent articles, the character or "feel" of such topsheets may be made undesirably altered by the presence of coated or impregnated acid. In addition, acidic material from such topsheets may be leached or abraded from the topsheet and delivered to the skin in a form which might cause undesirable comfort or safety problems.

In view of the foregoing it can be seen that there is a continuing need to identify improved disposable absorbent articles which are effective for absorbing discharged body waste and which also provide a desirable skin pH control benefit. The improved absorbent articles hereinafter described have such absorbency and skin pH control characteristics.

SUMMARY OF THE INVENTION

The present invention relates to an improved disposable absorbent articles such as diapers which tend to lower skin pH while absorbing discharged body fluids. Such articles comprise a liquid impervious backing sheet, a relatively hydrophobic, liquid pervious topsheet and a flexible absorbent core positioned between the backing sheet and the topsheet. The flexible absorbent core essentially contains hydrophilic fiber material and optionally contains particles of a substantially water-insoluble hydrogel material to increase the fluid absorbing capacity of the absorbent core.

The improvement in disposable articles of the foregoing type can be realized by constructing the relatively hydrophobic, liquid pervious topsheet at least in part from polymeric non-woven fabric or film material which contains acidic functional moieties in the structure of the polymers used to form the topsheet material. When such topsheets contain sufficient acidic functional moieties to impart an ion-exchange capacity to the topsheet of at least about 0.25 meq./gm., the topsheet can, upon exposure to body fluid, release protons in an amount sufficient to lower skin pH within the range of 3.0 to 5.5. As noted hereinbefore, lowering of skin pH to values within this acidic range has been found to be an important factor in preventing or at least reducing the incidence of diaper rash.

BRIEF DESCRIPTION OF THE DRAWING

The drawing submitted herewith represents a cutaway view of a disposable diaper which is a preferred configuration for the absorbent articles herein.

DETAILED DESCRIPTION OF THE INVENTION

The absorbent articles of the present invention can be manufactured in the configuration of wearable disposable products which are capable of absorbing significant quantities of water and body waste fluids such as urine, feces and menses. Thus such articles, for example, may be prepared in the form of disposable diapers, adult incontinence pads, sanitary napkins and the like.

The absorbent articles herein generally comprise three basic structural components. One such component is a liquid impervious backing sheet. On top of this backing sheet is placed an absorbent core which may itself comprise one or more distinct and/or separate zones or layers. On top of this absorbent core is placed a relatively hydrophobic, liquid pervious topsheet. The topsheet is the element of the article which is placed next to the skin of the wearer.

Especially preferred absorbent articles of this invention are disposable diapers. Absorbent articles in the form of disposable diapers are fully described in Duncan and Baker, U.S. Pat. No. Re. 26,151 Issued Jan. 31, 1967; Duncan, U.S. Pat. No. 3,592,194, Issued July 13, 1971; Duncan and Gellert, U.S. Pat. No. 3,489,148, Issued Jan. 13, 1970; and Buell, U.S. Pat. No. 3,860,003, Issued Jan. 14, 1975; which patents are incorporated herein by reference. A preferred disposable diaper configuration for use in the articles of this invention comprises an absorbent core; a liquid pervious topsheet superposed or co-extensive with one face of the core; and a liquid impervious backsheet superposed or co-extensive with the face of the core opposite the face covered by the topsheet. The backsheet most preferably has a width greater than that of the core thereby providing side marginal portions of the backsheet which extend beyond the core. Such a diaper is preferably constructed in an hourglass configuration.

No matter which configuration is used for the absorbent articles herein, the liquid impervious backing sheet and the absorbent core of the articles of this invention can be conventionally constructed. These elements are described in greater detail hereinafter. The present invention is based upon the use of an ion-exchanging topsheet in combination with such a backing sheet and absorbent core.

The ion-exchanging topsheets herein are those which release protons upon exposure to body fluids such as urine. Ion-exchange, i.e., proton release, characteristics can be imparted to fiber of film material used to form such topsheets by chemically modifying the polymer structure of the fiber or film to incorporate thereinto acidic functional moieties. Generally such chemical modification of polymeric fiber or film material will involve treatment of topsheet fiber or film with modifying agents which serve to incorporate carboxylic or inorganic acid functional groups into the polymer structure of the topsheet material.

Suitable chemically modified materials which can be used to form the topsheets of the absorbent articles herein include modified cellulosics such as cotton, rayon, ramie and the like; modified polyolefins such as low density polyethylene and polypropylene, modified polyesters and modified poly(acrylonitriles). Examples of particular materials of these types include oxidized cellulosics; phophorylated cellulosics; carboxymethylated cellulosics; succinylated cellulosics; grafts of polyolefins such as polypropylene with polyacrylics such as polyacrylic acid, hydrolyzed poly(acrylamides), polyacrylates, and poly(acrylonitriles); grafts of cellulosics with polyacrylics such as polyacrylic acid, hydrolyzed poly(acrylamides), polyacrylates and poly(acrylonitriles); sulfonated polyolefins; partially hydrolyzed poly(acrylonitriles) and partially hydrolyzed polyesters.

Especially preferred procedures for imparting ion-exchange properties to the topsheet material herein include the direct grafting by esterification of polyacrylic acid onto rayon/polyester fabric and the succinylation of such rayon/polyester fabric material. Direct grafting with polyacrylic acid involves the padding of solutions of polyacrylic acid onto rayon/polyester followed by baking to effect the esterification reaction. Suitable polyacrylic acid materials for this procedure are those ranging in molecular weight from about 2,000 to 5,000,000. Polyacrylic acid solutions used can range in polyacrylic acid content from about 0.1% to 10% by weight. Such solutions are applied to fabric in a weight ratio of polyacrylic acid to fabric of from about 0.02:1 to 2.0:1. Baking to effect esterification will generally occur at temperatures of from about 100° C. to 150° C. for a period of from about 10 to 60 minutes.

Succinylation of rayon/polyester blends can be carried out by treating the fabric to impregnate succinamic acid, $(H_2NOC)CH_2CH_2(COOH)$, followed by heating of the impregnated fabric to drive off ammonia and leave the succinylated fabric structure. Succinamic acid is generally applied to fabric in a mole ratio of succinamic acid to cellulose OH groups within the range of from about 0.25:1 to 2:1. Subsequent heating generally occurs at temperatures within the range of from about 100° C. to 150° C. for a period of from about 15 to 180 minutes.

No matter what procedure is employed to impart ion-exchange properties to the topsheet material used in the articles of the present invention, such topsheet material must be modified to the extent that the topsheets themselves have an ion-exchange capacity of at least about 0.25 meq./gram, preferably at least about 0.60 meq./gram, and most preferably at least about 1.0 meq./gram. Depending upon the type and concentration of modifying agents used to prepare the ion-exchange topsheet material, it may be necessary to carry out the chemical modification of the topsheet polymer material in several distinct treatment stages in order to reach the 0.25 meq./gram or higher desired ion-exchange capacity. It has been discovered that topsheets containing this relatively high concentration of acidic functional groups are especially effective for lowering skin pH to values within the requisite range of from about 3.0 to 5.5 in the presence of discharged body fluid. Preferably such topsheets serve to lower skin pH to within the range of from about 3.5 to 4.5. Also preferably such topsheets will maintain skin pH within the 3.0 to 5.5 range for the length of time the diaper is worn, e.g., for at least 4 hours for daytime diapers and for at least 8 hours for nighttime diapers.

The ion-exchanging topsheets herein can be prepared by modifying the topsheet fibers or films either before or after such materials have been fashioned into the finished topsheet substrate. In the case of fiber-containing topsheets, the topsheets may be constructed entirely of the modified ion-exchanging fibers or can be formed from both derivatized and non-derivatized fiber material.

Even though they are chemically modified to impart ion-exchange capacity thereto, the topsheets of the present absorbent articles must desirably remain relatively hydrophobic. For purposes of this invention, the liquid pervious topsheet is relatively hydrophobic if it is less absorbent of discharged body fluid than is the absorbent core placed beneath the topsheet.

As indicated, the ion-exchanging, liquid pervious topsheets hereinbefore described are used in combination with a liquid impervious backing sheet and a flexible absorbent core to form the absorbent articles of the present invention. The backing sheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The absorbent core is positioned between the backing sheet and the ion-exchanging topsheet to form the absorbent articles herein. Such an absorbent core essentially contains hydrophilic fiber material as the primary fluid-absobing medium. The type of hydrophilic fibers used in the absorbent core is not critical for use in the present invention. Any type of hydrophilic fiber which is suitable for use in conventional absorbent products is also suitable for use in the core of the absorbent articles of the present invention. Specific examples of such fibers include cellulose fibers, rayon, polyester fibers. Other examples of suitable hydrophilic fibers are hydrophilized hydrophobic fibers, such as surfactant-treated or silica-treated thermoplastic fibers. For reasons of availability and cost, cellulose fibers, in particular wood pulp fibers, are preferred.

In a preferred embodiment of the present invention, the absorbent core of the articles herein will also contain discrete particles of substantially water-insoluble hydrogel material. Such hydrogel materials are inorganic or organic compounds capable of absorbing fluids and retaining them under moderate pressures.

Suitable hydrogels can be inorganic materials such as silica gels or organic compounds such as cross-linked polymers. Cross-linking may be by covalent, ionic, van der Waals, or hydrogen bonding. Examples of hydrogel polymers include polyacrylamides, polyvinyl alcohol, ethylene maleic anhydride copolymers, polyvinyl ethers, hydroxpropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in Assarsson et al., U.S. Pat. No. 3,901,236, Issued Aug. 26, 1975, the disclosure of which is incorporated herein by reference. Particularly preferred hydrogel polymers for use herein are hydrolyzed acrylonitrile grafted starch, acrylic acid grafted starch, polyacrylates, and isobutylene maleic anhydride copolymers, or mixtures thereof.

Processes for preparing hydrogels are disclosed in Masuda et al., U.S. Pat. No. 4,076,663, Issued Feb. 28, 1978; in Tsubakimoto et al., U.S. Pat. No. 4,286,082, Issued Aug. 25, 1981; and further in U.S. Pat. Nos. 3,734,876, 3,661,815, 3,670,731, 3,664,343, 3,783,871, and Belgian Pat. No. 785,850, the disclosure of which are all incorporated herein by reference.

Hydrogel material is preferably used in the absorbent cores herein in the form of discrete particles. Hydrogel-containing cores will then be in the form of a web or batt of the hydrophilic fibers with the discrete particles of hydrogel dispersed therein. Hydrogel particles can be of any desired shape, e.g., spherical or semi-spherical, cubic, rod-like, polyhedral, etc. Shapes having a large greatest dimension/smallest dimension ratio, like needles, flakes and fibers, are also contemplated for use herein. Conglomerates of hydrogel particles may also be used.

Although hydrogel-containing absorbent cores used in preferred embodiments of the present invention are expected to perform well with hydrogel particles having a particle size varying over a wide range, other considerations may preclude the use of very small or very large particles. For reasons of industrial hygiene, (weight) average particle sizes smaller than about 30 microns are less desirable. Particles having a smallest dimension larger than about 2 mm may also cause a feeling of grittiness in the absorbent structure, which is undesirable from a consumer aesthetics standpoint. Preferred for use herein are particles having an (weight) average particle size of from about 50 microns to about 1 mm. "Particle Size" as used herein means the weight average of the smallest dimension of the individual particles.

The relative amount of hydrophilic fibers and hydrogel particles used in those absorbent articles herein which contain hydrogel can be most conveniently expressed in a weight ratio of fiber to hydrogel. These ratios may range from about 30:70 to about 98:2. For most commercially available hydrogels the optimum fiber/hydrogel ratio is in the range of from about 50:50 to about 95:5. Based on a cost/performance analysis, fiber/hydrogel ratios of from about 75:25 to about 90:10 are preferred. This preference is, of course, based on the relative costs of hydrophilic fibers (e.g. wood pulp fibers) and hydrogel. If, for example, wood pulp prices would go up and/or hydrogel prices would come down, lower fiber/hydrogel ratios would be more cost effective.

The density of the hydrogel-containing absorbent core can be of some importance in determining the absorbent properties of the resulting absorbent article. When hydrogel material is used in the absorbent core, the density of the absorbent core is preferably in the range of from about 0.10 to about 0.6 g/cm$^3$, and more preferably within the range of from about 0.12 to about 0.3 g/cm$^3$.

Absorbent cores containing hydrogel particles can be formed by airlaying a dry mixture of hydrophilic fibers and hydrogel particles. Such a procedure is described more fully in Procter & Gamble; European Patent Publication No. EP-A-122042; Published Oct. 17, 1984, incorporated herein by reference.

If hydrogel is employed in the absorbent core, it need not be uniformly distributed throughout the core. In fact, hydrogel can be placed only in one or more layers within the absorbent core, preferably near the bottom of the core. In such a case, the top portion of the absorbent core may consist essentially only of hydrophilic fiber material with substantially no hydrogel present.

The use of ion-exchanging topsheets for absorbent articles containing hydrogel particles in the absorbent core is especially advantageous. Many of the preferred hydrogel materials are most effective fluid absorbers when pH at the point of absorption is in the neutral to slightly alkaline range. Addition to absorbent articles of materials which lower pH can therefore adversely affect the fluid-absorbing capacity of the hydrogel. However, by utilizing an ion-exchanging topsheet to bring about desirable lowering of skin pH within the acid range, such acid pH effects tend to be more localized in the topsheet area which is remote from the hydrogel material. The absorbent capacity of the hydrogel material can thereby be preserved.

A preferred absorbent article in the form of a disposable diaper is illustrated by the drawing submitted herewith. The hourglass-shaped diaper structure of the drawing comprises a liquid impervious backing sheet 101. Positioned on top of the backing sheet 101 is an hourglass-shaped absorbent core 102 containing hydrophilic fiber material such as wood pulp fiber. Also distributed throughout the absorbent core 102 are discrete particles 103 of substantially water-insoluble, hydrogel material. Positioned on top of the hourglass-shaped absorbent core 102 is an ion-exchanging topsheet 104. Such a topsheet is constructed from fiber material such as succinylated rayon/polyester which provides the topsheet with an ion-exchange capacity of at least 0.25 meq./gram. Such a topsheet will deliver protons to the skin in the presence of body fluids such as urine so that skin pH is lowered to a value between about 3.0 and 5.5.

Absorbent articles using ion-exchanging topsheets are illustrated by the following examples:

EXAMPLE I

This example involves the direct esterification of a cellulosic fabric with polyacrylic acid to form absorbent article topsheets. Several solutions of polyacrylic acid (molecular weight=4,000,000) are padded on to sheets of 70%/30% rayon/polyester spunlaced fabric (Sontara ® by DuPont). These treated sheets are cured by baking for one hour in an oven at 110°–115° C. The cured fabrics are washed in distilled water to remove "free" polyacrylic acid and are then air dried. The several treating solutions, the amount of each employed and the resulting ion-exchange capacities imparted to the treated sheets are set forth in Table I.

TABLE I

| Sheet No. | Conc. of Polyacrylic Acid | Wgt Soln/ Wgt Cloth | Ion-Exchange Capacity |
|---|---|---|---|
| 1 | 0.2% | 4.2/1 | 0.14 meq/g |
| 2 | 0.5% | 4.7/1 | 0.13 meq/g |
| 3 | 0.5% | 25.6/1 | 0.90 meq/g |

Treated fabrics of these types are suitable for use as ion-exchanging topsheets provided their ion-exchange capacity exceeds 0.25 meq./gram. Thus Sheet Nos. 1 and 2 do not have sufficient ion exchange capacity after one treatment to serve as acceptable ion-exchanging topsheets within the context of the present invention. Additional treatments would be needed to increase the ion-exchange capacity of such sheets.

EXAMPLE II

A polypropylene topsheet taken from a commercially available diaper product LUVS is sulfonated with $SO_3$. In this procedure, as more fully described in Walles, U.S. Pat. No. 3,629,025, issued Dec. 21, 1971, the polypropylene material is treated with a refluxing solution of 3% $SO_3$ in methylenedichloride for one minute. After water washing and drying, the ion-exchange capacity of the topsheet is determined to be 0.38 meq/g.

EXAMPLE III

A cellulosic fabric is carboxymethylated with chloroacetic acid in this example. The fabric employed is the 70%/30% rayon/polyester Sontara ® used in Example I. Carboxymethylation is carried out in a series of steps which include: (1) reaction with NaOH to form alkali cellulose; (2) reaction with chloroacetic acid; (3) acidifcation in dilute HCl; (4) washing in distilled water; and (5) drying.

Several samples are prepared using various ratios of cellulosic to chloroacetic acid and various concentrations of the chloroacetic acid solution itself. In all cases, a 4.5/1 isopropyl alcohol/water solvent is used for both NaOH and chloroacetic acid. Also in all cases the molar ratio of NaOH to chloroacetic acid is maintained at 1.9/1. Reaction conditions and the ion-exchange capacities of the resulting fabric samples are shown in Table II.

TABLE II

| Sample No. | Cellulose*/ Chloroacetic Acid (Molar Ratio) | Chloroacetic Acid/Solvent Conc. (mM/ml) | Temp °C. | Time (Hrs) | Ion-Exchange Capacity (meq/g) |
|---|---|---|---|---|---|
| 1. | 2.47 | 0.34 | 50 | 3 | 0.12 |
| 2. | 0.52 | 1.70 | 50 | 2.5 | 0.44 |
| 3. | 0.33 | 0.30 | 50 | 4.5 | 0.09 |
| 4. | 0.33 | 1.24 | 65 | 4 | 0.28 |
| 5. | 0.33 | 1.04 | 65 | 2 | 0.56** |

*The MW of an anhydroglucose unit is used in this calculation.
** Reaction repeated once on same substrate to obtain this result.

Sample Nos. 2, 4 and 5 from Table II would be suitable for use as ion-exchanging topsheets in the articles herein.

EXAMPLE IV

In this example the 70%/30% rayon/polyester Sontara ® fabric is succinylated using succinamic acid. The Sontara ® fabric is impregnated with approximately 0.02 mole of succinamic acid in water per gram of fabric. The impregnated fabric is then heated in a forced-air oven for two hours at approximately 125° C. The fabric sample is then washed in dilute HCl followed by distilled water and is thereafter dried. Such a procedure provides a fabric suitable for use as a diaper topsheet having an ion-exchange capacity of about 1.5 meq/g.

EXAMPLE V

A carboxymethylated Sontara ® fabric as prepared in Example III is tested for its ability to control skin pH when used as a diaper topsheet in the presence of synthetic urine. In such testing, the carboxymethylated Sontara ® is substituted for the regular topsheet on patches (6.35 cm.×6.35 cm.) cut from a commercially available diaper product PAMPERS. Both these modified patches and unmodified patches cut from PAMPERS are soaked with six times their weight of a synthetic aqueous urine solution comprising 1.0% NaCl; 0.03% $CaCl_2.2H_2O$; 0.06% $MgCl_2.6H_2O$ and 0.0025% Triton X-100 nonionic surfactant. Such patches are then worn on the forearms of adult subjects for one hour, and skin pH values are then determined using a flat surface electrode. Results of such pH measurements are shown as follows.

| Standard Topsheet | Carboxymethylated Sontara$^R$ Sample No. 4 from Example III |
|---|---|
| Skin pH 5.50 | 4.50 |

EXAMPLE VI

Succinylated Sontara ® fabric as prepared in Example IV is tested as a diaper topsheet as follows. The succinylated fabric is used as a replacement topsheet in patches cut from PAMPERS as described in Example V. One such patch is soaked in five times its weight of the synthetic urine solution described in Example V. Another such patch is left dry. These patches are worn on the backs of adult subjects for one hour, and skin pH values are then measured using the flat surface electrode. Results are shown in Table III.

TABLE III

|  | Wet Patch | Dry Patch | Unpatched |
|---|---|---|---|
| Skin pH | 3.1 | 3.6 | 4.4 |

A diaper is prepared as described in Buell, U.S. Pat. No. 3,860,003, Issued Jan. 14, 1975. The hourglass-shaped softwood pulp core of such a diaper has the following dimensions: length: 15.5 in. (about 40 cm), width at the ears: 10.5 in. (about 27 cm), and width in the center: 3.75 in. (about 9.5 cm). The topsheet employed in such a diaper is a succinylated Sontara ® fabric prepared as described in Example IV. Such a topsheet has an ion-exchange capacity of 1.5 meq/g. Such a diaper is especially effective in lowering a baby's skin pH to within the range of 3.0–5.5 in the presence of urine discharged during use.

EXAMPLE VIII

A supplemental insert core containing fluid-absorbing hydrogel particles is added to the diaper structure of Example VII. Such s supplemental insert core is made with soft wood fibers and acrylic acid grafted starch hydrogel having a weight average particle size of about 25 microns ("Sanwet 1M-1000", from Sanyo Co., Japan) in a fiber:hydrogel ratio of 85:15. The supplemental insert core has a basis weight of 0.12 g/in. (0.019 g/cm$^2$) and a caliper of 0.03 in. (0.076 cm), which corresponds to a density of 0.25 g/cm$^3$. The supplemental insert core is covered with a sheet of envelope tissue and cut to a size of 3.5 in.×15.5 in. (about 9×40 cm). This supplemental insert core is inserted lengthwise into the diaper structure of Example VII in between the hourglass-shaped core and the polyethylene backing sheet, the envelope tissue being against the hourglass-shaped core.

The ion-exchanging succinylated topsheet in such a diaper is able to provide effective skin pH control while minimizing the lowering of the pH of fluid in the environment of the hydrogel-containing core. Absorbent capacity of the hydrogel in the insert core is thus not significantly diminished by the presence of the succinylated topsheet.

EXAMPLE IX

Several diaper patches are prepared using various types of absorbent cores and topsheets. These diaper patches are described in Table IV.

TABLE IV

| Patch No. | Core | Topsheet |
|---|---|---|
| 1. | 100% wood pulp fiber | Polypropylene (8 mil) |
| 2. | 80% wood pulp fiber 20% cross-linked polyacrylate hydrogel* (75% neutralized) | Polypropylene (8 mil) |
| 3. | 80% wood pulp fiber 20% acidified cross-linked polyacrylate hydrogel (34% neutralized) | Polypropylene (8 mil) |
| 4. | 80% wood pulp fiber 20% acidified cross-linked polyacrylate hydrogel (11% neutralized) | Polypropylene (8 mil) |
| 5. | 100% wood pulp fiber | Succinylated rayon/polyester** (Ion-exchange capacity = 0.9 meq/g) |

*Aqualic 4R04K1 from Nippon Shokubai K.K. Co. Ltd., Japan
**Sontara$^R$ from DuPont The 75% neutralized hydrogel in such structures serves to enhance fluid absorption capacity of the diaper. The acidified hydrogel acts as a pH control agent by releasing protons upon contact with urine. Such acidified hydrogels also provide some fluid absorbing capacity.

Patches such as described in Table IV are loaded with five times their weight of the synthetic urine solution described in Example V and are then worn on the forearms of adult subjects for two hours. Skin pH readings are then taken for each sample using a flat surface electrode. Results are set forth in Table V.

TABLE V

| Patch No. | Skin pH |
|---|---|
| 1 | 5.21 |
| 2 | 5.01 |
| 3 | 5.06 |
| 4 | 4.34 |
| 5 | 3.76 |

It can be seen from the Table V data that the diaper containing a succinlyated ion-exchanging topsheet is able to lower skin pH significantly better than are the diaper patches containing no ion-exchanging topsheet and even better than diaper patches containing acidified hydrogel material.

What is claimed is:

1. In a disposable absorbent article suitable for absorbing discharged body fluids while tending to lower skin pH, said article comprising a liquid impervious backing sheet, a relatively hydrophobic, liquid pervious topsheet and a flexible absorbent core containing hydrophilic fiber material, said absorbent core being positioned between said backing sheet and said topsheet, the improvement which comprises constructing said relatively hydrophobic topsheet at least in part from polymeric non-woven fabric or film material which in its polymer structure contains acidic moieties in an amount sufficient to impart an ion-exchange capacity of at least about 0.25 meq/g to said topsheet such that said topsheet, upon exposure to discharged body fluid, releases protons in an amount which is effective to lower skin pH to within the range of from about 3.0 to 5.5.

2. An article according to claim 1 wherein the topsheet material is selected from the group consisting of oxidized cellulosics, phosphorylated cellulosics, carboxymethylated cellulosics, succinylated cellulosics, grafts of polyolefin with polyacrylic acid or its derivatives, grafts of cellulosics with polyacrylic acid or its derivatives, sulfonated polyolefins, partially hydrolyzed acrylonitriles and partially hydrolyzed polyesters.

3. An article according to claim 2 wherein the ion-exchange capacity of the topsheet is at least about 1.0 meq./gram.

4. An article according to claim 2 wherein the topsheet material is a succinylated cellulosic fabric prepared by heating the cellulosic fabric with succinamic acid using a molar ratio of succinamic acid to cellulose OH groups of from about 0.25:1 to 2:1.

5. An article according to claim 4 wherein the cellulosic fabric comprises a blend of rayon and polyester.

6. An article according to claim 2 wherein the topsheet material is a graft of cellulosic fabric with polyacrylic acid and is prepared by reacting cellulose with polyacrylic acid in a weight ratio of polyacrylic acid to fabric of from about 0.02:1 to 2:1.

7. An article according to claim 2 wherein the flexible absorbent core additionally comprises particles of substantially water-insoluble hyrdogel material in a weight ratio of hydrophilic fiber to hydrogel of from about 30:70 to 98:2.

8. In a disposable diaper suitable for absorbing discharged body fluids while also reducing or preventing the incidence of diaper rash, said disposable diaper comprising a liquid impervious backing sheet, a relatively hydrophobic, liquid pervious topsheet and a flexible absorbent core containing hydrophilic fiber material, said absorbent core being positioned between said backing sheet and said topsheet, the improvement which comprises constructing said relatively hydrophobic topsheet at least in part from polymeric non-woven fabric or film material which in its polymer structure contains acidic functional moieties in an amount sufficient to impart an ion-exchange capacity of at least about 0.6 meq/g to said topsheet such that said topsheet, upon exposure to urine, releases protons in an amount which is effective to lower skin pH to within the range of from about 3.0 to 5.5.

9. A diaper according to claim 8 wherein the flexible absorbent core additionally comprises particles of substantially water-insoluble hydrogel material in a weight ratio of hydrophilic fiber to hydrogel of from about 50:50 to 95:5.

10. An article according to claim 8 wherein the topsheet material is selected from the group consisting of oxidized cellulosics, phosphorylated cellulosics, carboxymethylated cellulosics, succinylated cellulosics, grafts of polyolefins with polyacrylic acid or its derivatives, grafts of cellulosics with polyacrylic acid or its derivatives, sulfonated polyolefins, partially hydrolyzed acrylonitriles and partially hydrolyzed polyesters.

11. A diaper according to claim 10 wherein
(A) the cellulosic fabric comprises a blend of rayon and polyester,
(B) the topsheet has an ion-exchange capacity of at least about 0.6 meq./gram.

12. A diaper according to claim 10 wherein the topsheet material is a succinylated cellulosic fabric prepared by heating the cellulosic fabric with succinamic acid using a molar ratio of succinamic acid to cellulose OH groups of from about 0.25:1 to 2:1.

13. A diaper according to claim 10 wherein the topsheet material is a graft of cellulosic fabric esterified with polyacrylic acid and is prepared by reacting cellulose with polyacrylic acid in a weight ratio of polyacrylic acid to fabric of from about 0.02:1 to 2:1.

14. A disposable diaper suitable for absorbing discharged body fluids while also preventing or reducing diaper rash, said diaper comprising
(A) a liquid impervious backing sheet;
(B) a flexible absorbent core positioned on top of said backing sheet, said core comprising
 (i) hydrophilic fiber material; and
 (ii) particles of substantially water-insoluble hydrogel material; and
(C) a relatively hydrophobic, liquid pervious topsheet positioned on top of said flexible absorbent core, said topsheet being constructed at least in part from polymeric, non-woven fabric or film material selected from oxidized cellulosics, phosphorylated cellulosics, carboxymethylated cellulosics, succinylated cellulosics, grafts of polyolefins with polyacrylic acid or its derivatives, grafts of cellulosics with polyacrylic acid or its derivatives, sulfonated polyolefins, partially hydrolyzed acrylonitriles and partially hydrolyzed polyesters, said topsheet having an ion-exchange capacity of at least about 0.6 meq./g such that said topsheet, upon exposure to urine, releases protons in an amount effective to lower skin pH to within the range of from about 3.0 to 5.5.

15. A diaper according to claim 14 wherein the hydrogel material in the absorbent core is selected from hydrolyzed acrylonitrile grafted starch, acrylic acid grafted starch, polyacrylates, isobutylene maleic anhydride copolymers and mixtures of these hydrogels and wherein said hydrogel material is present in an amount such that the weight ratio of hydrophilic fiber to hydrogel ranges from about 50:50 to 98:2.

16. A diaper according to claim 15 wherein the ion-exchange capacity of the topsheet is at least about 1.0 meq./gram.

17. A diaper according to claim 15 wherein the topsheet material is a succinylated cellulosic fabric prepared by heating the cellulosic fabric with succinamic acid using a molar ratio of succinamic acid to cellulose OH groups of from about 0.25:1 to 2:1.

18. A diaper according to claim 17 wherein the cellulosic fabric comprises a blend of rayon and polyester.

19. A diaper according to claim 15 wherein the topsheet material is a graft of cellulosic fabric esterified with polyacrylic acid and is prepared by reacting cellulose with polyacrylic acid in a weight ratio of polyacrylic acid to fabric of from about 0.02:1 to 2.0:1.

20. A diaper according to claim 15 wherein the absorbent core is hourglass-shaped.

* * * * *